United States Patent [19]

Ince et al.

[11] Patent Number: 4,791,216

[45] Date of Patent: Dec. 13, 1988

[54] PARA ETHYL AMINO PHENOL PHARMACEUTICAL COMPOUNDS

[75] Inventors: Francis Ince; Alan C. Tinker, both of Loughborough, Great Britain

[73] Assignee: Fisons plc, Leicestershire, England

[21] Appl. No.: 938,249

[22] Filed: Dec. 5, 1986

Related U.S. Application Data

[62] Division of Ser. No. 662,348, Oct. 18, 1984, Pat. No. 4,657,929.

[30] Foreign Application Priority Data

Oct. 25, 1983 [GB] United Kingdom ............... 8328489
Oct. 25, 1983 [GB] United Kingdom ............... 8328490

[51] Int. Cl.$^4$ ................. C07C 147/06; C07C 103/85; C07C 87/28
[52] U.S. Cl. ...................................... 560/39; 558/234; 558/236; 558/413; 558/422; 560/40; 560/42; 564/165; 564/355
[58] Field of Search ............... 558/413, 422, 234, 236; 564/355, 165; 560/39, 40, 42

[56] References Cited

U.S. PATENT DOCUMENTS

| | | | |
|---|---|---|---|
| 3,202,711 | 8/1965 | Fruhstorfer et al. | 524/248 |
| 3,933,913 | 1/1976 | Colella et al. | 564/165 |
| 3,959,369 | 5/1976 | Smith | 564/165 |
| 4,115,409 | 9/1978 | Large et al. | 564/165 |
| 4,146,638 | 3/1979 | Renth et al. | 564/165 |
| 4,396,627 | 8/1983 | Airsworth et al. | 560/42 |
| 4,478,849 | 10/1984 | Airsworth et al. | 564/165 |

*Primary Examiner*—Veronica P. Hoke
*Attorney, Agent, or Firm*—Marshall, O'Toole, Gerstein, Murray & Bicknell

[57] ABSTRACT

There are provided paraethylamine phenol compounds of formula I,

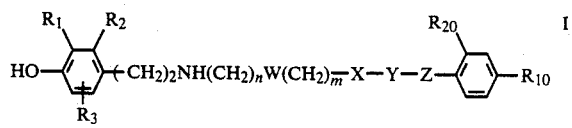

and pharmaceutically acceptable derivatives thereof.

There are also described the use of the compounds of formula I as pharmaceuticals, methods for making the compounds and pharmaceutical, e.g. cardiac, compositions containing the compounds.

9 Claims, No Drawings

PARA ETHYL AMINO PHENOL PHARMACEUTICAL COMPOUNDS

This is a division of application Ser. No. 662,348 filed Oct. 18, 1984, now U.S. Pat. No. 4,657,929.

This invention relates to new compounds, processes for their preparation and compositions containing them.

According to the invention we provide the compounds of formula I,

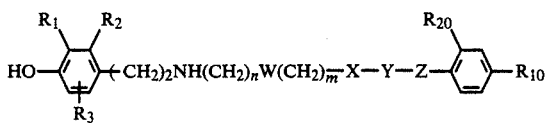

in which $R_1$ represents $NR_{11}R_{21}$, $CH_2R_{12}$, or fluorine, when $R_1$ represents $CH_2R_{12}$ or fluorine, $R_2$ and $R_3$, which may be the same or different, each independently represent hydrogen, fluorine, chlorine, bromine, alkyl C1 to 6, nitro, nitrile, $(CH_2)_pR_9$ or $SR_9$, when $R_1$ represents $NR_{11}R_{21}$, $R_{11}$ represents hydrogen, CHO, $COR_{13}$, $COOR_{13}$, $CONH_2$, $SO_2R_{13}$, $CH_2R_{14}$ or alkyl C1 to 6 and $R_{21}$ represents hydrogen and $R_2$ and $R_3$ are as defined above, or $R_{11}$ and $R_2$ together form the chain $=CR_{23}-CH=CH-$ in which the carbon bearing $R_{23}$ is adjacent to the nitrogen, $R_{23}$ represents hydrogen or hydroxy, $R_3$ is as defined above and $R_{21}$ has no meaning, or $R_{11}$ and $R_2$ together form the chain $-COCH_2-$ in which $-CO-$ is adjacent to the nitrogen, $R_3$ is as defined above and $R_{21}$ represents hydrogen, or $R_{11}$ and $R_2$ together represent 1,2-phenylene, $R_3$ is as defined above, and $R_{21}$ represents hydrogen, $R_{12}$ represents hydrogen, OH, $SO_2R_{13}$ or alkyl C1 to 6, $R_{13}$ represents alkyl C1 to 6, $R_{14}$ represents phenyl or alkoxy C1 to 6 phenyl, W represents a single bond, a 1,2; 1,3; or 1,4-disubstituted benzene ring; a $-CH=CH-$group or a 1,4-cyclohexanediyl group;

X represents NH, O, S, $SO_2$, CO, $CH_2$, CONH or $-COO$;

Y represents $(CH_2)_q$, CO, CS, $SO_2$ and $R_{20}$ represents hydrogen, or Y represents $CR_{15}R_{16}CR_{17}R_{18}$, wherein the carbon atom bearing $R_{15}$ and $R_{16}$ is adjacent to X and in which $R_{17}$ and $R_{18}$, together with the carbon atom to which they are attached form a carbonyl group, and $R_{15}$, $R_{16}$ and $R_{20}$ each represent hydrogen, or $R_{15}$ and $R_{20}$ together form a chain $-CH_2-$, and $R_{16}$, $R_{17}$ and $R_{18}$ each represent hydrogen, or $R_{15}$, $R_{16}$, $R_{17}$ and $R_{18}$ each independently represent hydrogen or alkyl C1 to 6 and $R_{20}$ represents hydrogen;

Z represents a single bond, $NR_{19}$, $CH_2$, O, CO, S or $SO_2$, in which $R_{19}$ represents hydrogen or alkyl C1 to 6;

n, and m each independently represent an integer from 1 to 4 inclusive;

q represents an integer from 1 to 3 inclusive;

p represents 0 or an integer from 1 to 3 inclusive;

$R_9$ represents phenyl or phenyl substituted by hydroxy, and $R_{10}$ represents hydrogen or chlorine, provided that (i) when X represents $SO_2$, CO, COO or CONH, then Y does not represent CO, CS or $SO_2$;

(ii) when Y represents CO, CS or $SO_2$, then Z does not represent CO or $SO_2$, and pharmaceutically acceptable derivatives thereof.

The invention also provides the compounds of formula I and their pharmaceutically acceptable derivatives, as pharmaceuticals.

According to our invention we also provide a process for the production of a compound of formula I, or a pharmaceutically acceptable derivative thereof, which comprises removal of at least one protecting group from a compound of formula II,

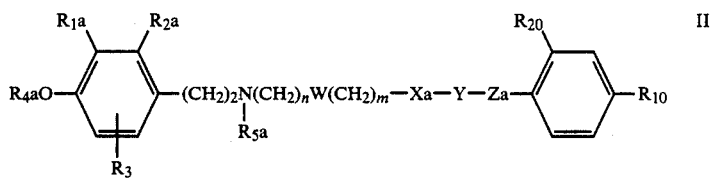

in which $R_3$, $R_{10}$, $R_{20}$ n, m, W and Y are as defined above, $R_{4a}$ and $R_{5a}$, which may be the same or different, each represent hydrogen or a protecting group, $R_{1a}$, $R_{2a}$, Xa and Za have the same respective meanings as $R_1$, $R_2$, X and Z defined above, save that in addition $R_{1a}$ represents $NR_{11a}R_{21a}$ or $CH_2OR_{7a}$, in which $R_{7a}$ and one or both of $R_{11a}$ and $R_{21a}$ may represent a protecting group, $R_{11a}$ and $R_{21a}$ otherwise being defined as $R_{11}$ and $R_{21}$ above, respectively;

Xa may represent $NR_{8a}$, in which $R_{8a}$ represents a protecting group,

Za may represent $NR_{19a}$, in which $R_{19a}$ has the same meaning as $R_{19}$ defined above, save that in addition, $R_{19a}$ may represent a protecting group, provided that the compound of formula II bears at least one protecting group, and where desired or necessary converting the resulting compound of formula I to a pharmaceutically acceptable derivative thereof, or vice versa.

Protecting groups that $R_{4a}$, $R_{5a}$, $R_{7a}$, $R_{8a}$, $R_{11a}$, $R_{19a}$ and $R_{21a}$ may represent include, for example, alkyl C1 to 6, especially methyl; phenylalkyl C7 to 12, especially benzyl; alkanoyl C2 to 6, such as acetyl, and haloalkanoyl C2 to 6, especially trifluoroacetyl. In addition, the protecting group may protect two functional groups, for example, $R_{4a}$ and $R_{7a}$ may together represent $(CH_3)_2C$. Other protecting groups are well known and include those described in Protective Groups in Organic Chemistry, ed: J W F McOmie, Plenum Press (1973), and Protective Groups in Organic Synthesis, T W Greene, Wiley-Interscience (1981).

Removal of the protecting group depends on the nature of the protecting group; conventional techniques may generally be employed, including acidic or basic cleavage or hydrogenolysis. For example, protecting alkyl or phenylalkyl groups may be removed by cleavage using a protic acid, e.g. hydrochloric acid or hydrobromic acid at a temperature of from 0° to 150° C., or a Lewis acid, e.g. by reacting with boron trihalide in a halocarbon solvent. When the protecting group is alkanoyl or haloalkanoyl, cleavage may be effected using a base, e.g. sodium hydroxide, in a suitable solvent, e.g. aqueous ethanol. Lewis bases, e.g. pyridine hydrochloride, may be used to cleave alkyl or phenylalkyl groups. 1-Phenylalkyl groups, e.g. benzyl, may be removed by catalytic hydrogenation using a suitable catalyst, e.g. palladium, in a suitable solvent, e.g. ethanol, or acetic acid. Further methods for the removal of protecting groups are described in both McOmie and Greene, loc. cit. Both McOmie and Greene also described numerous methods for the application of protecting groups.

When none of Xa, Y or Za represents CO, CS, COO, CONH or $SO_2$, compounds of formula II may be made by reducing a compound of formula III,

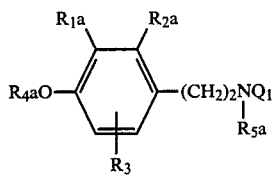

in which
  one or both of $Q_1$ and $Q_2$ represents CO, and the other represents $CH_2$,
  and $R_{1a}$, $R_{2a}$, $R_3$, $R_{4a}$, $R_{5a}$, $R_{10}$, $R_{20}$, W, Xa, Y, Za, n and m are as defined above.

The reducing agent may be electrophilic, for example diborane, or nucleophilic, for example, a complex metal hydride such as lithium aluminium hydride or sodium (2-methoxyethoxy)aluminium hydride. The reaction may be carried out in a suitable solvent inert to the reaction conditions. Aprotic solvents are preferred, for example tetrahydrofuran, diethyl ether or 1,2-dimethoxyethane. The reaction may be carried out at a temperature of, for example, from 0° to 100° C.

When Xa represents $NR_{8a}$, the compounds of formula III may be made by sequentially reacting the groups $L_1$ and $L_2$, in any order of the corresponding compound of formula IV, $$L_1Q_1-(CH_2)_{n-1}W(CH_2)_{m-1}Q_2L_2 \quad\quad IV$$

in which one of $L_1$ and $L_2$ represents a good leaving group and the other of $L_1$ and $L_2$ represents either a good leaving group or a group which may be readily converted into a good leaving group, and W, n, m, $Q_1$ and $Q_2$ are as defined above,
with the compounds of formula V and formula VI,

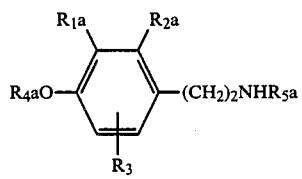

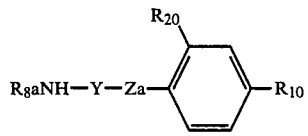

in any order,
wherein $R_{1a}$, $R_{2a}$, $R_3$, $R_{4a}$, $R_{5a}$, $R_{8a}$, $R_{10}$, $R_{20}$, Y, and Za are as defined above.

Good leaving groups that $L_1$ and $L_2$ may represent include, for example, halogen, e.g. chlorine or bromine; 1-imidazolyl, trifluoromethanesulphonate; alkyl carbonate, e.g. ethyl carbonate, benzyl carbonate; alkanoyloxy, e.g. acetoxy, or trifluoroacetoxy.

The displacement reactions may be carried out in a solvent which is inert to the reaction conditions, for example, a chlorinated hydrocarbon, e.g. chloroform, in the presence of a non-nucleophilic base, e.g. triethylamine. The reaction may be carried out at a temperature of from about 0° to 100° C.

The free acids of compound IV, i.e. those compounds in which both $L_1$ represents —OH and $Q_1$, represents CO, and/or both $L_2$ represents —OH and $Q_2$ represents CO may be reacted, e.g. with thionyl chloride, ethyl chloroformate, or N,N'-carbonyldiimidazole to convert the carboxyl groups to a group —$COL_1$ or —$COL_2$ respectively.

When $L_1$ and/or $L_2$ represent a group which may be converted into a good leaving group, such convertable groups include alkoxy, e.g. ethoxy or methoxy; and hydroxy. The conversion may be effected using conventional techniques.

An example of a sequential replacement of $L_1$ and $L_2$ is as follows:

A compound of formula IV in which $L_1$ represents $OCH_3$, $L_2$ represents OH and both $Q_1$ and $Q_2$ represent CO is reacted with a compound of formula VI in dichloromethane, at 0° C. with N,N'-carbonyldiimidazole, to give the compound of formula VII,

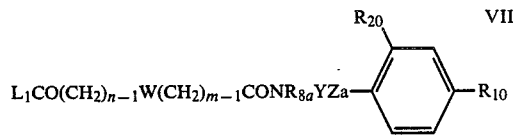

in which $L_1$ represents $OCH_3$, and $R_{8a}$, $R_{10}$, $R_{20}$, n, m, W, Y, and Za are as defined above:

Saponification of the —$COL_1$ group with one equivalent of base, followed by acidification gives the corresponding compound of formula VII with $L_1$ representing —OH, which can be reacted with the appropriate compound of formula V in the presence of N,N'-carbonyldiimidazole to give the desired compound of formula III.

Using analogous processes, the following compounds may be produced:

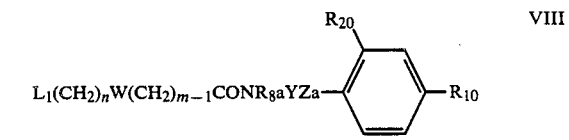

-continued

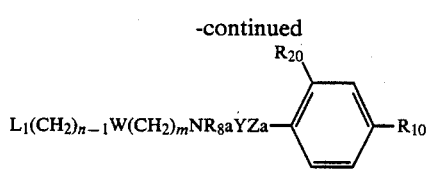

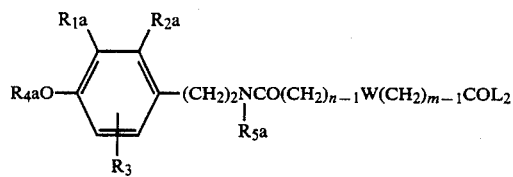

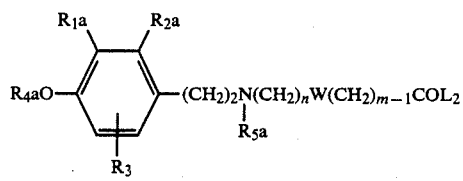

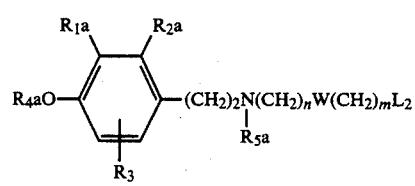

in which $R_{1a}$, $R_{2a}$, $R_3$, $R_{4a}$, $R_{5a}$, $R_{8a}$, $R_{10}$, $R_{20}$, $L_1$, $L_2$, n, m, W, Y, and Za are as defined above.

Similarly, compounds of formula II in which Xa represents $CH_2$ may be made be reacting a compound of formula XIII,

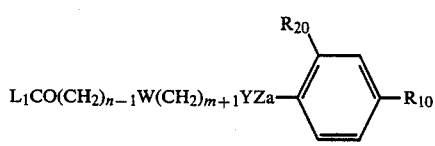

in which $R_{10}$, $R_{20}$, $L_1$, n, m, W, Y and Za are as defined above, with an appropriate compound of formula V. For example, with $L_1$ representing OH, the compound of formula XIII may be reacted with the compound of formula V to give a compound of formula II in the presence of N,N'-carbonyldiimidazole.

Compounds of formula II may also be made by reacting a corresponding compound of formula XIV,

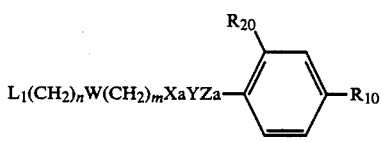

in which $R_{10}$, $R_{20}$, n, m, W, Xa, Y, Za and $L_1$ are as defined above,
with a compound of formula V as defined above.

The reaction is preferably carried out in the presence of a base. As a specific example, $L_1$ may represent bromine, $R_{5a}$ may represent trifluoroacetyl the reaction being carried out in dimethylformamide in the presence of sodium hydride.

Compounds of formula XIV in which Xa represents S or O may be made by reacting a compound of formula XV,

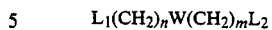   XV in which $L_1$, $L_2$, n, m, and W are as defined above, with a compound of formula XVI,

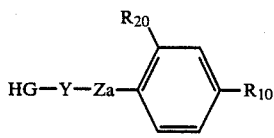

in which G represents O or S and $R_{10}$, $R_{20}$, Y and Za are as defined above.

The reaction is preferably carried out in the presence of a base, e.g. sodium hydride, in an aprotic, polar solvent, e.g. dimethylformamide.

Compounds of formula II in which Xa represents S or O may also be prepared by reacting the corresponding compound of formula XII as defined above with a compound of formula XVI as defined above, preferably in the presence of a base, e.g. sodium hydride, in an inert solvent, e.g. a polar, aprotic solvent such as dimethylformamide.

Compounds of formula II, in which Xa and Z each represent NH and Y represents CO may be prepared by reacting a compound of formula XVII,

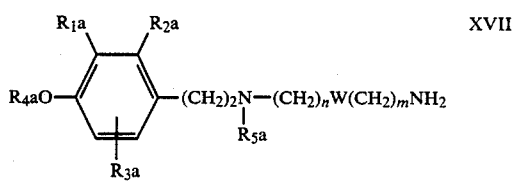

in which $R_{1a}$, $R_{2a}$, $R_3$, $R_{4a}$, $R_{5a}$, n, m and W are as defined above,
with a compound of formula XVIII,

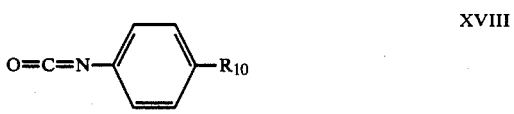

in which $R_{10}$ is as defined above.

The reaction may be carried out in an inert solvent, e.g. toluene at a temperature of from about 0° to 100° C. or in the absence of a solvent.

Compounds of formula XVII may be made from compounds of formula XI, e.g. by conversion of $L_2$ from —$OCH_3$ to —OH to $NH_2$, followed by reduction of the —CO— group by conventional techniques.

Compounds of formula II in which Xa represents NH, Y represents CO and Za represents $CH_2$ or a single bond may be prepared by reacting a compound of formula XVII as defined above with a compound of formula XIX,

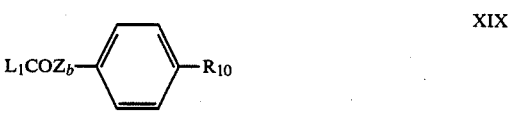

in which $Z_b$ represents $CH_2$ or a single bond and $L_1$ and $R_{10}$ are as defined above. The reaction is preferably carried out in the presence of a non-nucleophilic base, e.g. triethylamine, in a solvent which is inert to the reaction conditions, e.g. dichloromethane.

Compounds of formula II in which one or more of $X_a$, Y or $Z_a$ represent $SO_2$ or $R_{1a}$ represents $CH_2SO_2R_{13}$ may be prepared by selectively oxidising the corresponding compound of formula II in which $X_a$, Y or $Z_a$ represents S or $R_{1a}$ now represents $CH_2SR_{13}$. Suitable oxidising agents include inorganic and preferably organic peracids, e.g. m-chloroperbenzoic acid. The oxidations may be carried out in a solvent inert to the reaction conditions, e.g. dichloromethane, at a temperature of from 0° to 100° C.

Compounds of formula II, in which $X_a$ represents —CONH or —COO may be prepared by reacting the corresponding compound of formula XX,

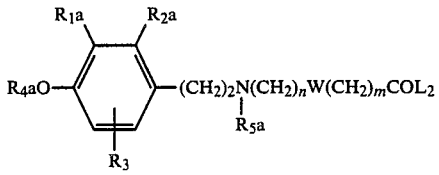

in which $R_{1a}$, $R_{2a}$, $R_3$, $R_{4a}$, $R_{5a}$, n, m, $L_2$ and W are as defined above,
with a compound of formula XXI,

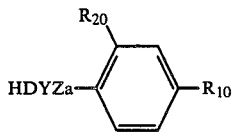

in which D represents O or NH, and $R_{10}$, $R_{20}$, Y and Za are as defined above.

The reaction is preferably carried out by in situ conversion of a compound of formula XX in which $L_2$ represents —OH to an activated mixed anhydride by reaction with, e.g. ethyl chloroformate in the presence of base, followed by reaction with the compound of formula XXI to produce the compound of formula II. The reaction is preferably carried out in solvent inert to the reaction conditions, for example dichloromethane.

The compounds of formula XXI may be prepared by methods analagous to those described above for the compounds of formula XI.

Compounds of formula V in which $R_{1a}$ represents $CH_2OH$ may be prepared by reacting the corresponding compound of formula XXII,

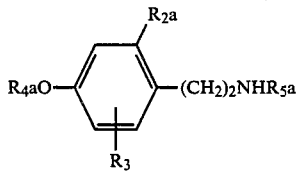

wherein
$R_{2a}$, $R_3$, $R_{4a}$ and $R_{5a}$ are as defined above,
with dichloromethylmethylether in the presence of a Lewis acid catalyst, e.g. $TiCl_4$ in an inert solvent, e.g. dichloromethane at a temperature of from $-78°$ to 50° C., followed by reduction of the resultant aldehyde derivative with a selective reducing agent, e.g. sodium borohydride.

Compounds of formula V in which $R_{1a}$ represents $CH_2SR_{13}$ may be prepared by reacting the corresponding compound of formula XXII with a compound of formula XXIII, $R_{13}SCH_2Cl$             XXIII in which $R_{13}$ is as defined above,
in the presence of a Lewis acid, e.g. $SnCl_4$ in an inert solvent, e.g. dichloromethane, at a temperature of from 0 to 50° C.

Compounds of formula V in which $R_{1a}$ represents $NHR_{11}$ in which $R_{11}$ represents alkyl C1 to 6 may be prepared from the corresponding compound of formula V in which $R_1$ a represents $NH_2$ by reaction with an alkyl C1 to 6 halide.

The reaction is preferably carried out in the presence of base, e.g. potassium carbonate, in a polar, aprotic solvent, for example, dimethylformamide.

Compounds of formula V in which $R_{1a}$ represents $NHR_{11}$ in which $R_{11}$ represents $CH_2R_{14}$, wherein $R_{14}$ is as defined above, may be prepared by reacting a corresponding compound of formula V in which $R_{1a}$ represents $NH_2$ with a compound of formula XXIV, $R_{14}CHO$             XXIV in which $R_{14}$ is as defined above, and reduction of the resulting imine.

The reaction may, for example, be carried out by refluxing in a high boiling solvent, e.g. toluene, with the continuous removal of water, followed by reduction with hydrogen using a platinum catalyst.

Compounds of formula V in which $R_{1a}$ represents $NR_{11}R_{21}$, and $R_{11}$ and $R_{2a}$ together form the chain $=CR_{23}$—CH=CH— in which the carbon bearing $R_{23}$ is adjacent to the nitrogen, $R_{23}$ represents hydroxy and $R_{21}$ has no meaning may be prepared by reacting a corresponding compound of formula V in which $R_{1a}$ represents $NH_2$ and $R_{2a}$ represents hydrogen, with the diethyl acetal of 3-oxopropanoic acid, in the presence of N,N'-carbonyldiimidazole in an inert solvent, followed by cyclisation of the resulting amide with acid, e.g. conc. sulphuric acid.

The remaining compounds of formula V, and the compounds of formulae IV, VI, XV, XVI, XVIII, XIX, XXII, XXIII and XXIV are either known or may be made from known compounds by conventional techniques, known per se.

The acid addition salts of the compounds of formula I may be prepared by reaction of the free-base with an appropriate acid. The acid addition salts may be converted to the corresponding free-base by the action of a stronger base.

The processes as described above may produce the compound of formula I or a derivative thereof. It is also within the scope of this invention to treat any derivative so produced to liberate the free compound of formula I, or to convert one derivative into another.

The compounds of formula I and the intermediates therefor may be isolated from their reaction mixtures using conventional techniques.

Pharmaceutically acceptable derivatives of the compounds of formula I include pharmaceutically acceptable acid addition salts. Suitable salts include salts of mineral acids, for example, hydrochloric acids, e.g.

hydrochloric acid or hydrobromic acid; or organic acids, e.g. formic, acetic or lactic acids. The acid may be polybasic, for example sulphuric, fumaric or citric acid.

Other pharmaceutically acceptable derivatives are compounds which will be suitable bioprecursors (pro-drugs) of the compounds of formula I and will be readily apparent to those skilled in the art and may be made from the compounds of formula I using conventional processes known per se or by processes analogous to those described above. Suitable bioprecursors include amides, e.g. acetamides or benzamides, of compounds of formula I, and esters, for example, carboxylic acid esters, e.g. alkanoyl, such as acetyl or isobutyryl, or aroyl C7-9, e.g. benzoyl, esters.

As a preferred group of compounds, we provide compounds of formula I in which $R_1$ represents $NR_{11}R_{21}$ or $CH_2R_{12}$, either $R_2$ represents hydrogen, $R_{11}$ represents hydrogen, CHO, $COR_{13}$, $COOR_{13}$, $CONH_2$, $SO_2R_{13}$, $CH_2R_{14}$ or alkyl C1 to 6 and $R_{21}$ represents hydrogen, or $R_2$ and $R_{11}$ together form the chain $=CR_{23}$—CH=CH—, in which the carbon bearing $R_{23}$ is adjacent to the nitrogen, $R_{23}$ represents hydrogen or hydroxy, and $R_{21}$ has no meaning, or $R_2$ and $R_{11}$ together form the chain —$COCH_2$— in which —CO— is adjacent to the nitrogen, and $R_{21}$ represents hydrogen, or $R_2$ and $R_{11}$ together represent 1,2-phenylene, and $R_{21}$ represents hydrogen, or $R_2$ represents hydrogen and $R_{12}$ is as defined above, $R_3$ and $R_{20}$ each represent hydrogen, W and Z each represent a single bond, X represents NH, Y represents $(CH_2)_q$, and n, m, q, $R_{10}$, $R_{13}$ and $R_{14}$ are as defined above, and pharmaceutically acceptable derivatives thereof.

As a specific group of compounds, we provide compounds of formula I in which $R_1$ represents $NHR_{11}$ or $CH_2R_{12}$, $R_{11}$ represents hydrogen, CHO, $COR_{13}$, $COOR_{13}$, $CONH_2$, $SO_2R_{13}$, $CH_2R_{14}$ or alkyl C1 to 6, $R_2$, $R_3$ and $R_{20}$ each represent hydrogen, W and Z each represent a single bond, X represents NH, Y represents $(CH_2)_q$, and $R_{10}$, $R_{12}$, $R_{13}$, $R_{14}$, n, m and q are as first defined above, and pharmaceutically acceptable derivatives thereof.

As a second specific group of compounds, we also provide compounds of formula I in which $R_1$ represents $NR_{11}R_{21}$, either $R_{11}$ and $R_2$ together form the chain $=CR_{23}$—CH=CH— in which the carbon bearing $R_{23}$ is adjacent to the nitrogen, $R_{23}$ represents hydrogen or hydroxy, and $R_{21}$ has no meaning, or $R_{11}$ and $R_2$ together form the chain —$COCH_2$— in which —CO— is adjacent to the nitrogen, and $R_{21}$ represents hydrogen, or $R_{11}$ and $R_2$ together represent 1,2-phenylene and $R_{21}$ represents hydrogen;

$R_3$ and $R_{20}$ each represent hydrogen,

W and Z each represent a single bond,

Y represents $(CH_2)_q$, and $R_{10}$n, m and q are as first defined above, and pharmaceutically acceptable derivatives thereof.

We prefer the compounds in which $R_1$ represents $CH_2OH$, $NHCH_3$ or $NHSO_2CH_3$.

$R_2$, $R_3$, $R_{11}$, $R_{12}$, $R_{13}$, $R_{15}$, $R_{16}$, $R_{17}$ or $R_{18}$, when they represent alkyl C1 to 6 preferably contain up to and including four carbon atoms. Specific groups that $R_2$, $R_3$, $R_{11}$, $R_{12}$, $R_{13}$, $R_{15}$, $R_{16}$, $R_{17}$ or $R_{18}$ may represent include methyl, ethyl, n-propyl, isopropyl and tert-butyl.

We prefer $R_2$ and $R_3$ to be selected from hydrogen, fluorine, chlorine, bromine, $CH_2CH_2C_6H_5$ and $CH_2CH_2C_6H_4OH$. We particularly prefer compounds in which $R_2$ represents chlorine and $R_3$ represents hydrogen. We also particularly prefer compounds in which and $R_3$ represents fluoro.

$R_{14}$ preferably represents 4-alkoxy C1 to 6 phenyl, more preferably 4-methoxyphenyl.

We prefer compounds in which W represents a single bond.

We prefer compounds in which X represents NH. We also prefer compounds in which X represents O or S.

Y preferably represents $(CH_2)_q$. We also prefer compounds in which Y represents $CR_{15}R_{16}CR_{17}R_{18}$. We particularly prefer compounds in which

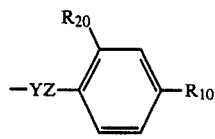

represents 2-indanyl.

Z preferably represents a single bond.

n and m each independently preferably represent 1, 2 or 3.

q preferably represents 1 or 2.

p preferably represents 0, 1 or 2.

When Z represents a single bond, we prefer the sum of n+m to be from 5 to 7 inclusive, especially 6.

The compounds of formula I, and pharmaceutically acceptable derivatives thereof, are useful because they possess pharmacological activity in animals. Thus the compounds act on peripheral and/or central dopamine receptors. As such, they lower blood pressure, reduce heart rate and increase blood flow to certain vascular beds, e.g. renal beds. Some compounds also have an action on other adrenoreceptors, and these exhibit cardiac stimulant and bronchodilator effects. Activity of the compounds has been observed in the following assay systems:

(a) canine renal blood flow, McNay and Goldberg, J. Pharmac, Exp. Ther., 151, 23–31, 1966.

(b) rabbit isolated ear artery, McCullogh, Rand and Story, Br. J. Pharmac, 49, 141–142, 1973, and (c) cat nictitating membrane, Gyorgy and Doda, Arch. Int. Pharmacodyn, 226, 194–206, 1977.

The compounds of the invention are indicated for use in the treatment of congestive heart failure, renal failure, angina pectoris, ischaemic heart disease, hypertension and reversible obstructive airways disease, hyperprolactinaemia and also in Parkinson's disease and other neurological disorders. Compounds of the invention are also indicated for use in the treatment of glaucoma, gastric hypersecretion, e.g. in peptic ulcers, premature labour, acromegaly, and improvement of the blood supply to and healing of intestinal anastomoses and stomata.

The dosage administered will naturally depend on the compound employed, the mode of administration and the desired effect. However, in general, satisfactory results are obtained when the compounds are administered at a dosage of from 0.05 μg to 50 mg per kilogram of body weight per day. For man, the indicated total daily dosage is in the range of 2.5 μg to 3.5 g, which may be administered in divided doses of, for example 1 μg to 750 mg.

The new compounds of the present invention may be used in combination with, or sequentially with, a wide variety of other pharmaceutically active substances. Where appropriate the compounds may be mixed with one or more other active substances. The particular mixture or dose regimen used, and ratio of the active ingredients will depend on a variety of factors including the condition to be treated, the mode of administration, the particular active ingredients and the patient concerned.

Examples of compounds with which the present compounds may be mixed include:
beta-blockers, especially cardioselective beta blockers, for example, atenolol;
diuretics, for example thiazides, e.g. furosemide;
angiotensin converting enzyme inhibitors, for example captopril;
inotropic agents, for example, amrinone;
antiemetics, for example, sulpiride, metoclopramide, or domperidone.

The compounds of formula I, and pharmaceutically acceptable derivatives thereof, have the advantage that they are more efficacious or produce less undesirable side effects in certain pharmacological models, or are longer acting than compounds of similar structure to the compounds of formula I.

The compounds of the invention may be administered by a wide variety of routes and may act systemically or locally. Thus the compounds may be administered by oral or nasal inhalation to the lung, to the buccal cavity, oesophageally, rectally, topically to the skin or to other available surfaces of the body, e.g. the eye, by injection, e.g. intravenously, intramuscularly, intraperitoneally, by instillation or by surgical implant.

According to our invention we also provide a pharmaceutical composition comprising preferably less than 80%, and more preferably less than 50%, by weight of a compound of formula I, or a pharmaceutically acceptable derivative thereof, in admixture with a pharmaceutically acceptable adjuvant, diluent or carrier. Examples of suitable adjuvants, diluents or carriers are: for tablets, capsules and dragées; microcrystalline cellulose, calcium phosphate, diatomaceous earth, a sugar such as lactose, dextrose or mannitol, talc, stearic acid, starch, sodium bicarbonate and/or gelatin;
for suppositories; natural or hardened oil or waxes; and
for inhalation compositions, coarse lactose.

When the compounds are to be used in aqueous solution it may be necessary to incorporate a chelating or sequestering agent, e.g. sodium edetate, an antioxidant, e.g. sodium metabisulphite or buffering agents, e.g. sodium hydrogen phosphate and sodium phosphate. Aqueous solutions typically contain up to about 10% w/w of the new compound and may be used for intravenous injections.

According to the invention, we further provide a method of increasing the force of contraction of the heart in an animal, either human or non-human, which method comprises administering to the animal an effective amount of one or more compounds of the invention.

The invention is illustrated, but in no way limited by the following Examples in which temperatures are in degrees Centigrade.

In general all compounds and intermediates are named in accord with "Naming and Indexing of Chemical substances for Chemical Abstracts", reprinted from Appendix IV of the Chemical Abstracts 1977 Index Guide.

In particular derivatives of hexanedioic acid, in which the carboxylic acid groups are in a 1,6-relation to one another, are named as hexanedioates, not 1,6-hexanedioates.

EXAMPLE 1

2-Hydroxy-5[2-(6-(2-phenylethylamino)hexylamino)ethyl] benzene methanol dioxalate (a)

2,2,2-Trifluoro-N-[2-(4-methoxyphenyl)ethyl]acetamide

4-Methoxybenzeneethanamine (50 g, 0.33 mole) was dissolved in dry dichloromethane (500 ml) cooled to −5° and a solution of trifluoroacetic anhydride (139 g, 93.6 ml, 0.66 mole) in dry dichloromethane (60 ml) was added dropwise with stirring under nitrogen. The reaction mixture was stirred at room temperature for 2 hr, evaporated to dryness and the residue recrystallised from cyclohexane to give a white solid (76.5 g); mp 82°–3°.

(b)

2,2,2-Trifluoro-N-(2(3-formyl-4-methoxyphenyl)ethyl acetamide

The product from step (a) (24.7 g, 0.1 mole) was dissolved in dry dichloromethane (500 ml) and the solution cooled to −15°. A solution of titanium tetrachloride (57.0 g, 21.6 ml, 0.3 mole) in dry dichloromethane (200 ml) was added dropwise with stirring and cooling. To the yellow-orange solution was added—dichloromethyl methyl ether (27.9 g, 22.0 ml, 0.24 mole) in dry dichloromethane (200 ml). The solution was stirred at −15° for 0.5 hr and warmed to room temperature over a period of 2 hr. The reaction mixture was poured onto ice/2N hydrochloric acid (21/500 ml) and stirred vigorously. The dichloromethane layer was separated and the aqueous layer extracted with dichloromethane (2×200 ml). The combined organic extracts were washed with water, dried ($Na_2SO_4$) and evaporated. The crude product was recrystallised from 50% aqueous methanol to give an off-white solid (24.0 g) mp 105°–6°.

(c)

2,2,2-Trifluoro-N-(2-(3-formyl-4-hydroxyphenyl)acetamide

The product from step (b) (9.65 g, 0.035 mole) was dissolved in dry chloroform (400 ml) and cooled to −78°. Boron tribromide (17.5 g, 6.6 ml, 0.07 mole) was added.

The mixture warmed to room temperature and stirred for 2 hr. Ice was added slowly followed by 2N hydrochloric acid and the mixture stirred vigorously for 18 hr. The chloroform layer was separated and the aqueous layer extracted with chloroform (2×200 ml). The combined organic extracts were washed with water, dried ($Na_2SO_4$) and evaporated. The residue was recrystallised from aqueous methanol to give a pale pink solid (4.96 g), mp 80°–2°.

(d)
2,2,2-Trifluoro-N-(2-(4-hydroxy-3-hydroxymethylphenyl) acetamide

The product from step (c) (5.6 g, 0.022 mole) was dissolved in 2-propanol (100 ml) and sodium borohydride (0.81 g, 0.022 mole) added in portions with stirring. Stirring was continued for 2 hr and the mixture heated to reflux for 1 hr, the majority of the 2-propanol was removed in vacuo and the residue diluted with water (200 ml), acidified with 2N hydrochloric acid and extracted with ether (3×100 ml). The combined extracts were washed with water and brine, dried (Na$_2$SO$_4$) and evaporated to give a white solid (4.8 g) mp 95°–7°.

(e)
N-2-(2,2-Dimethyl-1,3-benzodioxin-6-yl)ethyl-2,2,2-trifluoroacetamide The product from step (d) (5.22 g, 0.02 mole) was dissolved in 2,2-dimethoxypropane (50 ml) and p-toluenesulphonic acid (50 mg) added and the mixture stirred at room temperature for 2 hr. The mixture was diluted with ether (200 ml) and washed with saturated aqueous sodium bicarbonate solution (2×50 ml) and brine, dried (Na$_2$SO$_4$) and evaporated. The residue was recrystallised from cyclohexane to give the sub-title compound as a white solid (2.76 g,) mp 91°–3°.

(f)
N-2-(2,2-Dimethyl-1,3-benzodioxin-6-yl)ethyl-N'-2-phenylethyl-1,6-hexanediamine dioxalate The product from step (e) (2.74 g, 0.00904 mole) dissolved in dry dimethylformamide (15 ml) was added to a suspension of oil free sodium hydride (0.24 g, 0.01 mole) in dry dimethylformamide (15 ml) and the mixture stirred at room temperature for 1 hr. A solution of N-(6-Bromohexyl)-2,2,2-trifluoro-N-(2-phenylethyl)acetamide (3.43 g. 0.00904 mole) in dry dimethylformamide (10 ml) was added and the mixture heated at 75° for 3 hr. The reaction mixture was poured into water (400 ml) and extracted with ether (3×100 ml). The combined extracts were washed with water (3×) and brine, dried (Na$_2$SO$_4$) and evaporated affording a yellowish oil (5.7 g).

A portion of this oil (5.4 g) was dissolved in methanol (50 ml) and 5N sodium hydroxide solution (50 ml) added and the mixture heated to reflux for 3 hr. The majority of the methanol was removed in vacuo. The residue diluted with water (200 ml) and extracted with ethyl acetate (3×70 ml). The combined extracts were washed with water (2×) and brine, dried (Na$_2$SO$_4$) and evaporated to give an oil (3.76 g).

A portion of this oil (3.2 g) was dissolved in methanol (35 ml) and a solution of oxalic acid (1.42 g, 2 equivalents) in methanol (25 ml). The resulting solid was isolated and dried in vacuo to give a white solid (2.60 g,) mp 192°–5° (dec).

(g)
2-Hydroxy-5[2-(6-(2-phenylethylamino)hexylamino)ether] benzenemethanol dioxalate The product from step (f) (2.60 g, 0.0044 mole) was heated on a steam bath in water (60 ml) under nitrogen for 2 hr. The water was removed in vacuo and the residue recrystallised from water (30 ml) to give the dioxalate salt of the title compound, (1.25 g, 52%) mp 187° (dec).

EXAMPLE 2
2-Methylsulphonylmethyl-5-[2-(6-(2-phenylethylamino) hexylamino)ethyl]phenol dihydrobromide

(a)
2,2,2-Trifluoro-N-(2-(4-methoxy-3-methylthiomethyl phenyl)ethylacetamide The product from Example 1 step (a) (24.7 g, 0.1 mole) was dissolved in dry dichloromethane (200 ml). To this solution was added chloromethyl methylsulphide (8.4 ml, 0.1 mole) followed by a solution of stannic chloride (23.4 ml, 0.2 mole) in dry dichloromethane (200 ml) and the solution was stirred at room temperature for 4 hr. The reaction mixture was poured into 2N hydrochloric acid (11), the dichloromethane separated and the aqueous layer extracted with dichloromethane (2×200 ml). The combined extracts were washed with water, dried (Na$_2$SO$_4$) and evaporated. The residue was recrystallised from cyclohexane to give the sub-title compound as a white solid (23.2 g); mp 101°–103°.

(b)
N[2-(4-Methoxy-3-methylsulphonylmethylphenyl)ethyl] N-(2-phenylethyl)-1,6-hexanediamine dihydrochloride The product from step (a) (6.8 g, 0.022 mole) dissolved in dry dimethylformamide (30 ml) was added slowly to a suspension of oil free sodium hydride (0.55 g, 0.023 mole) in dry dimethylformamide (30 ml) and the mixture stirred at room temperature for 2 hr. To this solution was added N-(6-bromohexyl)-2,2,2-trifluoro-N-(2-phenylethyl)acetamide (8.8 g, 0.023 mole) dissolved in dry dimethylformamide (20 ml) and the resulting mixture heated to 80° for 6 hr. The reaction mixture was poured into water (900 ml), 2N hydrochloric acid (100 ml) added and extracted with ether (3×300 ml). The combined extracts were washed with water (4×) and brine, dried (Na$_2$SO$_4$) and evaporated to give a yellow oil (14.0 g) (MS; m/e 606).

This oil was dissolved in dichloromethane (650 ml) and 3-chloroperoxybenzoic acid (8.8 g, 0.05 mole) added in portions with cooling (ice bath) and stirring. Stirring was continued for 2 hr at room temperature after which time the reaction mixture was washed with saturated aqueous sodium bicarbonate solution (2×300 ml) and water, dried (Na$_2$SO$_4$) and evaporated to give an oil (19.0 g). This oil was chromatographed on silica gel (510 g) using ether-petroleum ether mixtures as eluant, to give an oil (7.6 g) (MS; M$^+$+1, m/e 639, M$^+$—SO$_2$CH$_3$ m/e 559).

This oil was dissolved in methanol (100 ml) and a solution of sodium hydroxide (1.25 g, 0.031 mole) in water (20 ml) added and the mixture heated to reflux for 2 hr. The majority of the methanol was removed in vacuo and the residue diluted with water and extracted with ethyl acetate (3×100 ml). The combined extracts were washed with water (2×) and brine, dried (Na$_2$SO$_4$) and evaporated. The residue was dissolved in ethyl acetate (50 ml) and a saturated solution of hydrogen chloride gas in ether (200 ml) added. The solvents were removed in vacuo and the residue recrystallised from methanol to give a white solid (4.38 g,); mp 249°–52°.

(c)
2-Methylsulphonylmethyl-5[2-(6-(2-phenylethylamino)hexylamino)ethylphenol dihydrobromide The product from step (b) (4.35 g, 0.0084 mole) was heated to reflux for 4 hr under nitrogen with 48% aqueous hydrobromic acid (100 ml). The acid was removed in vacuo and the residue recrystallised from ethanol to give a white solid (2.9 g,); mp 189°–92°.

EXAMPLE 3

N-[2-hydroxy-5-[2-(6-(2-phenylethylamino)hexylamino] ethyl]phenyl]methanesulphonamide (a)
2,2,2-Trifluoro-N-[2-(3-methanesulphonylamino-4-methoxy phenyl)ethyl]acetamide Methanesulphonyl chloride (5.75 g, 0.05 moles) in dry dichloromethane (50 ml) was added dropwise with stirring to N-[2-(3-amino-4-methoxyphenyl)ethyl]-2,2,2-trifluoro acetamide (13.1 g, 0.05 moles) and triethylamine (10.1 g, 7.5 ml, 0.1 mole) in dry dichloromethane (250 ml). Stirring was continued at 20° for 18 hr and the solution was then washed with dilute hydrochloric acid, saturated sodium bicarbonate solution and water, dried and evaporated. The residue on recrystallisation from benzene gave the sub-title compound (15.9 g) as ivory-coloured plates mp 129°–130°.

(b)
N-[5-(2-Aminoethyl)-2-methoxyphenyl]methanesulphonamidehydrochloride

The product from step (a) (15.6 g, 0.046 moles) and potassium carbonate (6.33 g, 0.046 moles) in methanol (270 ml) and water (30 ml) were boiled at reflux for 4 hr. Evaporation of the solvents afforded a gum which was extracted with several portions of hot ethyl acetate. Evaporation of the extracts gave an oil which on treatment with ethanolic hydrogen chloride afforded the sub-title compound as white crystals (10.5 g) mp 181°–183°.

(c)
N-[2-(3-Methanesulphonylamino-4-methoxyphenyl)-ethyl]-N'-(2-phenylethyl)hexanediamide N,N'-carbonyldiimidazole (3.25 g, 0.02 moles) was added in portions under nitrogen to a suspension of 6-oxo-6-(2-phenylethylamino)hexanoic acid (4.98 g, 0.02 moles) in dry dichloromethane (100 ml). The mixture was stirred for 30 mins, the product from step (b) (5.6 g, 0.02 moles) and triethylamine (2.8 ml, 2.02 g, 0.02 moles) were added, and stirring continued for a further 4 hr. The precipitate was collected and the filtrate washed with dilute hydrochloric acid and aqueous sodium bicarbonate solution and evaporated. The residue and the original precipitate were combined and recrystallised from methanol giving the sub-title compound (6.6 g) as white needles mp 193°–195°.

(d)
N-[2-Methoxy-5-[2-[6-(2-phenylethylamino)hexylamino]ethyl]phenyl]methaneslphonanide hydrochloride Method I
Boron trifluoride etherate (4.0 ml, 4.6 g, 32.5 mmole) in dry tetrahydrofuran (20 ml) was added dropwise with stirring to a suspension of sodium borohydride (1 g, 26.3 m mole) and the product from step (c) (3.2 g, 6.7 mmoles) in dry tetrahydrofuran under nitrogen. When addition was complete the suspension was heated at reflux for 4 hr, then cooled in ice and treated with methanol (25 ml). The mixture was filtered, the filtrate evaporated to dryness and the residue treated with methanol (100 ml) saturated with hydrogen chloride gas for 3 hr. The white solid was collected and washed with cold methanol and dry ether giving the sub-title dihydrochloride (3.4 g) mp 249°–251° (decomp.).

Method II
The product of step (b) (0.7 g, 2.5 mmole), N-(6-bromohexyl)-2,2,2-trifluoro-N-(2-phenylethyl)acetamide (0.95 g, 2.5 mmole) and triethylamine (0.5 g, 5 mmole) in dry dimethylformamide (10 ml) were heated at 100° for 5 hr. The solution was poured into water (50 ml) and extracted with ethyl acetate. The extracts were washed with water, dried and evaporated to an oil (1 g), which was boiled under reflux with potassium carbonate (0.50 g) in methanol (20 ml) and water (5 ml) for 3 hr. The solvent was evaporated and the residue extracted with ethyl acetate. The extracts were evaporated to dryness and the residue dissolved in ethanolic hydrogen chloride. Addition of an equal volume of dry ether afforded a white solid (0.45 g) identical with that produced by Method I above.

(e)
N-[2-Hydroxy-5-[2-[6-(2-phenylethylamino)hexylamino]ethyl]phenyl]methanesulphonamide dihydrobromide The product of step (d) (3.38 g, 6.5 mmoles) and triethylamine (2.0 ml, 1.45 g, 14.4 mmoles) in dry dichloromethane (100 ml) were stirred for 30 minutes and the suspension obtained was cooled to −60° and boron tribromide (2.5 ml, 6.6 g, 26 mmole) added dropwise under nitrogen. The mixture was kept at −50° or below for 1 hr and then at 20° for 18 hr, before methanol (25 ml) was cautiously added. The precipitate was collected and recrystallised from water giving the title compound dihydrobromide (2.4 g) as colourless needles mp 251°–252°.

EXAMPLE 4

2-Amino-4-[2-[6-(2-phenylethylamino)hexylamino]ethyl]phenol

N-[2-[3-Amino-4-methoxyphenyl]ethyl]-2,2,2-trifluoro acetamide (2.62 g, 0.01 moles) in dry dimethylformamide (50 ml) was added dropwise with stirring to sodium hydride (0.3 g., 80% oil dispersion, 0.01 moles) in dry dimethylformamide (50 ml) under nitrogen. The solution was warmed at 60° for 30 min then cooled and N-(6-bromohexyl)-2,2,2-trifluoro-N-(2-phenylethyl-)acetamide (3.80 g., 0.01 mole) was added. The solution was stirred for 4 hours then quenched with water and extracted with ethyl acetate. The extracts were washed with water dried and evaporated to give crude N-[2-(3-amino-4-methoxyphenyl)ethyl]-N'-(2-phenylethyl)-1,6-hexanediylbis (2,2,2-trifluoroacetamide) (3.1 g) as a pale brown oil.

This crude product (3.0 g) in 48% hydrobromic acid (30 ml) and hypophosphorous acid (0.5 ml) was boiled at reflux under nitrogen for 7 hr. The solution was cooled, filtered from precipitated tar and evaporated. The residue was recrystallised from ethanol-ether and from 2-propanol to give the title compound trihydrobromide (1.5 g) as off-white crystals mp 253°–255° (decomp).

EXAMPLE 5

2-(Methylamino)-4-[2-[6-(2-phenylethylamino)hexylamino]ethyl]phenol (a)

2,2,2-trifluoro-N-[2-[-4-methoxy-3-(methylamino)-phenyl]ethyl]acetamide

N-[2-[3-Amino-4-methoxyphenyl]ethyl]-2,2,2-trifluoro acetamide (26.2 g., 0.1 mole) and iodomethane (14.0 g., 6.2 ml., 0.1 mole) in dry dimethylformamide (500 ml) were stirred under nitrogen for 3 hr. The solution was poured into water and the suspension extracted with ethyl acetate. Evaporation of the extracts afforded an oil which was separated by high pressure liquid chromatography on silica using 1% methanol in dichloromethane as eluant. Evaporation of the fractions containing the major bond afforded the sub-title compound (6.1 g) as a white solid mp 65°–67°. The hydrochloride, prepared in the usual way, had mp 153°–155°.

(b) 4-Methoxy-3-(methylamino)benzeneethanamine

The product from step (a) (4.14 g) and potassium carbonate (2.07 g) in methanol (100 ml) and water (10 ml) was boiled, at reflux for 4.5 hr. The solution was evaporated to dryness and the residue partitioned between chloroform and water. Evaporation of the organic phase afforded an orange oil which solidified on standing to give the sub-title compound as crystals (2.7 g) mp 90°–92°.

(c)

N-[2-[4-Methoxy-3-(methylamino)phenyl]ethyl]-N'-(2-phenylethyl)-1,6-hexanediamide This was prepared from the product of step (b) (2.2 g) by the procedure of Example 3(c). The sub-title compound was obtained as a colourless solid (3.8 g) mp 173°–4°.

(d)

N-[2-[4-methoxy-3-(methylamino)phenyl]ethyl]N'-(2-phenylethyl)-1,6-hexanediamine This was prepared from the product of step (c) (2.4 g) using the procedure of example 3(d) Method I. The sub-title compound was obtained as the trihydrochloride (1.3 g), a fawn solid (MS m/e 383) used without purification in the next step.

(e)

2-(Methylamino)-4-[2-[6-(2-phenylethylamino)hexylamino]ethyl]phenol trihydrobromide This was prepared from the product of step (d) above (1.0 g) using the procedure of example 2(c). The title-compound, as the trihydrobromide salt, was recrystallised twice from 2-propanol as colourless crystals (0.7 g) of the hemihydrate mp 165°–167°.

EXAMPLE 6

4-[2-[6-(2-Phenylethylamino)hexylamino]ethyl]-2-(phenylmethylamino)phenol (a)

2,2,2-Trifluoro-N-[2-[4-methoxy-3-(phenylmethyleneamino)phenyl]ethyl]acetamide

N-[2-[3-Amino-4-methoxyphenyl]ethyl]-2,2,2-trifluoro acetamide (10.48 g., 40 mmoles) and benzaldehyde (4.24 g., 40 mmoles) in toluene (150 ml) was heated at reflux with a Dean-Stark water separator for 3 hrs. The toluene was evaporated leaving a yellow oil (14 g). Prolonged trituration with light petroleum afforded the sub-title compound as a pale yellow solid (11.9 g) mp 49°–52°.

(b)

2,2,2-trifluoro-N-[2-[4-methoxy-3-(phenylmethylamino)phenyl]ethyl]acetamide

The product from step (a) (11.9 g) and platinum oxide (0.2 g) in ethanol (150 ml) was hydrogenated at room temperature and 3 atmospheres pressure for 18 hrs. The catalyst was filtered and the ethanol evaporated to afford the crude product as a red oil (12 g). This was purified by flash chromatography on silica using petroleum ether/ethyl acetate (3.1) as eluant. Evaporation of the major fraction eluted afforded sub-title compound as white crystals (6.1 g) mp 80°–82°.

(c)

4-Methoxy-3-(phenylmethylamino)benzeneethanamine

This was prepared from the product of step (b), (5.7 g) using the procedure of example 27(b). The sub-title compound was obtained as an oil (3.0 g) (m.s. m/e 236) which was used directly in the following step.

(d)

N-[2[4-Methoxy-3-(phenylmethylamino)phenyl]ethyl]-N'-(2-phenylethyl)-1,6-hexanediamide This was prepared from the product of step (c) (1.65 g) using the procedure of example 3(c). The sub-title compound was obtained as a solid mp 167°–169° (1.65 g).

(e)

N-[2-[4-Methoxy-3-(phenylmethylamino)phenyl]ethyl]-N'-(2-phenylethyl)-1,6-hexanediamine trihydrochloride The product of step (d) (1.65 g) and diborane (34 ml of 1M solution in tetrahydrofuran) in dry tetrahydrofuran (100 ml) was boiled at reflux for 14 hr. Excess diborane was destroyed by cautious addition of methanol and the solution was evaporated to dryness. The residue was dissolved in methanol (50 ml) and concentrated hydrochloric acid (5 ml) and boiled at reflux for 2 hr. Evaporation of the solution gave a solid which after trituration with ether and recrystallisation from ethanol gave the sub-title compound (0.65 g) mp 245°–7°.

(f)

4-[2-[6-(2-Phenylethylamino)hexylamino]ethyl]-2-(phenylmethylamino)phenol trihydrobromide This was made from the product of (e) (0.6 g) using procedure of example 3(e). The title compound, as the trihydrobromide salt, (0.45 g) was obtained as crystals from 2-propanol mp 166°–168°.

EXAMPLE 7

N-[2-Hydroxy-5-[2-[6-(2-phenylethylamino)hexylamino]ethyl]phenyl]acetamide dihydrobromide (a)

N-[2-[3-(Acetylamino)-4-methoxyphenyl]ethyl]-2,2,2-trifluoroacetamide

N-[2-(3-Amino-4-methoxyphenyl)ethyl]-2,2,2-trifluoro acetamide (5.24 g., 0.02 moles) in acetic anhydride (20 ml) was boiled at reflux for 2 hr. The anhydride was removed under reduced pressure and the syrupy residue added to water. The grey solid was collected and recrystallised from toluene using charcoal to give the sub-title compound as cream crystals (4.0 g) mp 105°–106°.

(b) N-[5-(2-aminoethyl)-2-methoxyphenyl]acetamide

This was prepared from the product of step (a) (3.95 g) using the procedure of example 3(b). The hydrochloride of the sub-title compound (1.8 g), was obtained as white crystals from ethanol mp 200°–202°.

(c) N-[2-Methoxy-5-[2-[6-(2-phenylethylamino)hexylamino]ethyl]phenyl]acetamide dihydrochloride This was prepared from the product of step (b) (1.8 g) using the procedure described in example 3(d) (Method II). The sub-title compound was obtained as colourless crystals from methanol (0.8 g) mp 232°–234°.

(d) N-[2-Hydroxy-5-[2-[6-(2-phenylethylamino)hexylamino]ethyl]phenyl]acetamide dihydrobromide This was prepared from the product of step (c) (0.7 g) using the procedure of example 3(e). The title compound was obtained as colourless crystals from water (0.4 g) mp 260°–262°.

EXAMPLE 8

2-Fluoro-4-[2-[6-(2-phenylethylamino)hexylamino]ethyl]phenol (a) N-[2-[3-Fluoro-4-methoxyphenyl]ethyl]N'-(2-phenylethyl)hexanediamide This was prepared from 3-fluoro-4-methoxybenzene ethanamine (2.05 g., 0.01 mole) using the procedure of Example 25(c). The sub-title compound (2.7 g) formed colourless needles mp 173.5°–175.5°.

(b) N-[2-(3-Fluoro-4-methoxyphenyl)ethyl]-N'-2-phenylethyl)-1,6-hexanediamine dihydrochloride This was prepared from the product of step (a) above (2.68 g) using the procedure of example 3(d) (Method I). The sub-title compound (2.55 g) was obtained as plates from methanol mp 305°–307°.

(c) 2-Fluoro-4-[2-[6-(2-phenylethylamino)hexylamino]ethyl]phenol dihydrobromide

The product from step (b) (1.8 g) in 48% hydrobromic acid (18 ml) containing hypophosphorous acid (10 drops) was boiled at reflux under nitrogen for 5.5 hr. The solid which separated on cooling the solution was collected and recrystallised from water giving the dihydrobromide salt of the title compound as colourless needles (1.3 g) mp 240.5°–242.5°.

EXAMPLE 9

N-(6-Bromohexyl)-2,2,2-trifluoro-N-(2-phenylethyl)acetamide 2,2,2-Trifluoro-N-(2-phenylethyl)acetamide (21.7 g., 0.1 mole) in dry dimethylformamide (100 ml) was added dropwise with stirring and under nitrogen to sodium hydride (2.4 g., 0.1 mole, ether washed) in dry dimethylformamide (150 ml). Stirring was continued until a clear solution was obtained and 1,6-dibromohexane (73.2 g., 0.3 moles) was added. The solution was heated at 60° for 3 hr then poured into water and extracted with ether. The extracts were washed well with water and dried and evaporated. Excess dibromohexane was recovered by distillation (b.p. 60°–70°/0.1 mmHg) and the residue was separated on a silica gel column using ether-light petroleum (1:2) as eluant. The major fraction was evaporated to give the title compound as a pale yellow oil (24 g). A sample was distilled to give a colourless viscous liquid, b.p. 146°–152°/0.05 mmHg, (with slight decomposition).

EXAMPLE 10

1,2-Dihydro-8-hydroxy-5-[2-[6-(2-phenylethylamino)hexylamino]ethyl]-2-oxo-2H-quinoline (a) 3,3-Diethoxy-N-[2-methoxy-5-[2-(2,2,2-trifluoroacetylamino)ethyl]phenyl]propanamide N,N'-Carbonyldiimidazole (10 g, 62 mmoles) was added over 5 minutes under nitrogen to 3,3-diethoxypropanoic acid (10 g, 62 mmoles) in dry dichloromethane (150 ml). The solution was stirred for 30 minutes and N-[2-(3-Amino-4-methoxyphenyl)ethyl]-2,2,2-trifluoroacetamide (16.1 g, 62 mmoles) in dry dichloromethane (150 ml) was then added dropwise. Stirring was continued for 4 h and the solution was washed with dilute hydrochloric acid, sodium bicarbonate solution and water. Evaporation gave a brown oil which solidified on trituration with petrol. Recrystallisation from petroleum ether (b.p. 60°–80°) gave the sub-title diamide as white fluffy needles (18.6 g) mp 79°–80°.

(b) N-[2-(1,2-Dihydro-8-methoxy-2-oxo-5-quinolinyl)ethyl]-2,2,2-trifluoroacetamide The product of (a) (17.0 g, 42 mmoles) was added cautiously to concentrated sulphuric acid (50 ml) with stirring. When the addition was complete the dark solution was heated at 100° for 45 min then cooled and poured into ice-water. The suspension was extracted with ethyl acetate, and the extracts washed with sodium bicarbonate solution and water, dried and evaporated to give the sub-title compound as a pale yellow solid (11.0 g) mp 181°–184°. A sample recrystallised from ethanol-cyclohexane formed colourless needles mp 185°–186°.

(c) 5-(2-Aminoethyl)1,2-dihydro-8-methoxy-2-oxo-2H-quinoline

The product of step (b) (11.0 g, 35 mmoles) and potassium carbonate (9.68 g, 70 mmoles) in methanol (200 ml) and water (30 ml) were boiled at reflux for 3 hr. The methanol was evaporated under reduced pressure and the aqueous residue was neutralised by dropwise addition of acetic acid. The pale yellow crystals which separated were filtered and washed with cold water and cold ethanol giving the sub-title compound (free base) as a hydrate (8 g) mp ca. 130° (decomp). This was dissolved in hot ethanol and treated with conc. hydrochloric acid (5 ml). The colourless crystals which separated on cooling the solution were filtered and washed with cold ethanol and ether giving the sub-title compound (hydrochloride) (5.8 g) mp 253°–255° (decomp).

(d) 1,2-Dihydro-8-methoxy-5-[2-[6-(2-phenylethylamino)hexylamino]ethyl]-2-oxo-2H-quinoline The hydrochloride from step (c) (2.55 g, 0.01 mole), N-(6-bromohexyl)-2,2,2-trifluoro-N-(2-phenylethyl)acetamide (3.80 g, 0.01 mole), potassium iodide (1.66 g, 0.01 mole) and triethylamine (2.0 g, 1.8 ml, 0.02 mole) in dry dimethyl formamide (25 ml) were heated at 100° under nitrogen for 4 hrs. Water (200 ml) was added and the suspension extracted with ethyl acetate. The extracts were washed with water, dried and evaporated giving the crude N$^6$-trifluoroacetyl derivative of the sub-title compound as an oil (4.1 g).

The crude oil (4.0 g, 7.7 mmole), and potassium carbonate (2.2 g, 16 mmoles) in water (20 ml) and methanol (100 ml) was boiled at reflux for 3 hrs. The methanol was then removed under vacuum and the aqueous residue was extracted with ethyl acetate. The extracts were evaporated leaving an oil which was dissolved in ethanol (100 ml) and treated with concentrated hydrochloric acid (1.5 ml, 16.5 mmoles). The solution was taken to dryness leaving a pinkish solid which on recrystallisation from ethanol gave the sub-title compound dihydrochloride (1.9 g) as colourless crystals mp 264°–267° (decomp).

(e)

1,2-Dihydro-8-hydroxy-5-[2-[6-(2-phenylethylamino)-hexylamino]ethyl]-2-oxo-2H-quinoline dihydrobromide The product from step (d) (1.2 g, 2.5 mmoles) in 48% aqueous hydrobromic acid (12 ml) containing hypophosphorous acid (0.1 ml) was boiled under reflux under nitrogen for 5 hrs. The hydrobronic acid was evaporated and the yellow solid residue was triturated for 20 minutes with dry ethanol (50 ml) during which time the yellow colour faded and a white solid separated. This solid (1.3 g) was filtered and recrystallised from ethanol-water, giving the title compound dihydrobromide as small colourless prisms mp 293°–295° (dec).

What we claim is:

1. A compound of formula I,

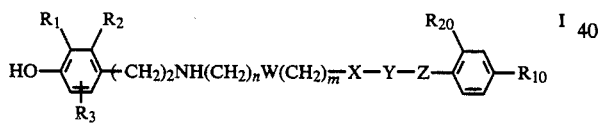

in which $R_1$ represents $CH_2R_{12}$, or fluorine;

$R_2$ and $R_3$, which may be the same or different, each independently represent hydrogen, fluorine, chlorine, bromine, alkyl $C_1$ to $C_6$, nitro, nitrile, $(CH_2)_pR_9$ or $SR_9$;

$R_{12}$ represents hydrogen, OH, $SO_2R_{13}$ or alkyl $C_1$ to $C_6$, $R_{13}$ represents alkyl $C_1$ to $C_6$, W represents a single bond, a 1,2; 1,3; or 1,4-disubstituted benzene ring; a —CH=CH— group or a 1,4-cyclohexanediyl group;

X represents NH, O, S, SO$_2$, CO, CH$_2$, CONH or —COO;

Y represents $(CH_2)_q$, CO, CS, SO$_2$ and $R_{20}$ represents hydrogen, or Y represents $CR_{15}R_{16}CR_{17}R_{18}$, wherein the carbon atom bearing $R_{15}$ and $R_{16}$ is adjacent to X and in which $R_{17}$ and $R_{18}$, together with the carbon atom to which they are attached from a carbonyl group, and $R_{15}$, $R_{16}$, $R_{17}$ and $R_{18}$ each represent hydrogen, or $R_{15}$, $R_{16}$, $R_{17}$ and $R_{18}$ each independently represent hydrogen or alkyl $C_1$ to $C_6$ and $R_{20}$ represents hydrogen;

Z represents a single bond, $NR_{19}$, $CH_2$, O, CO, S or SO$_2$, in which $R_{19}$ represents hydrogen or alkyl $C_1$ to $C_6$;

n, and m each independently represent an integer from 1 to 4 inclusive;

q represents an integer from 1 to 3 inclusive;

p represents 0 or an integer from 1 to 3 inclusive;

$R_9$ represents phenyl or phenyl substituted by hydroxy, and $R_{10}$ represents hydrogen or chlorine, provided that (i) when X represents SO$_2$, CO, COO or CONH, Y does not represent CO, CS or SO$_2$;

(ii) when Y represents CO, CS or SO$_2$, then Z does not represent CO or SO$_2$, and pharmaceutically acceptable derivatives thereof.

2. A compound according to claim 1, wherein $R_2$ and $R_3$ are selected from hydrogen, fluorine, chlorine and bromine.

3. A compound according to claim 1, wherein W represents a single bond.

4. A compound according to claim 1, wherein X represents NH, O or S.

5. A compound according to claim 1 wherein Y represents $(CH_2)_q$.

6. A compound according to claim 1, wherein $R_1$ is $CH_2R_{12}$, $R_3$ and $R_{20}$ each represent hydrogen, W and Z each represent a single bond, X represents NH, and Y represents $(CH_2)_q$.

7. A compound according to claim 1 which is 2-Hydroxy-5[2-(6-(2-phenylethylamino)hexylamino)ethyl]benzene methanol;

or a pharmaceutically acceptable salt thereof.

8. A compound according to claim 1 which is selected from the group consisting of:

2-Methylsulphonylmethyl-4-[2(6-(2-phenylethylamino)hexylamino)ethyl]phenol;

2-Fluoro-4-[2-[6-(2-phenylethylamino)hexylamino]ethyl]phenol;

and pharmaceutically acceptable salts thereof.

9. A compound according to claim 1 in which $R_1$ is $CH_2R_{12}$.

* * * * *